United States Patent [19]

Schwartz, deceased

[11] Plant 4,291

[45] Aug. 15, 1978

[54] ROSE PLANT

[75] Inventor: Ernest Schwartz, deceased, late of Kingsville, Md., by Hazel E. Schwartz, executrix

[73] Assignee: F. Harmon Saville Nor'East Miniature Roses, Rowley, Mass.

[21] Appl. No.: 854,510

[22] Filed: Nov. 25, 1977

[51] Int. Cl.[2] ..... A01H 5/00

[52] U.S. Cl. ..... Plt./7

[58] Field of Search ..... Plt./7

*Primary Examiner*—Robert E. Bagwill
*Attorney, Agent, or Firm*—Vincent G. Gioia

[57] ABSTRACT

A novel rose variety of the miniature rose class characterized by high centered, heavy petalled, coral pink blooms substantially as shown and described.

1 Drawing Figure

1

The present invention relates to a new and distinct variety of rose plant of the miniature rose class, which was originated by my crossing as seed parent the floribunda rose known as "Zorina" and an unnamed seedling as pollen parent.

Among the novel characteristics possessed by this new variety which distinguish it from its parents and all other varieties of which I am aware are: (1) high centered blooms of coral pink coloring, (2) flowers borne singly and in full sprays of as many as 5 to 7 florets, (3) heavily petaled flowers with petals reflexing and quilling symmetrically on opening and (4) blooms of lasting quality on the plant and after cutting. Asexual reproduction by budding of the new variety as performed in Essex County, Mass., shows that the foregoing and other distinguishing characteristics come true to form and are established and transmitted through succeeding propagations.

The new and improved rose variety which I have developed is a fine miniature rose with unusual heavy petalage but nevertheless high centered form also blooming both in sprays and single blooms to a stem. The flowers are unusually heavily petaled, for a miniature rose, having as many as 50 to 55 petals which on opening reflex and quill symmetrically in a pleasing manner.

Despite this heavy petalage, the blooms are supported well on sturdy erect peduncles. The plant itself is upright compact growing and is vigorous with uniform branching.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "43C" is plate 43C of the Royal Horticultural Society Color Chart.

Parentage: Seedling.
*Seed parent.*—"Zorina" (floribunda).
*Pollen parent.*—"Unnamed Seedling".
Class: Miniature.

2

The following observations are made of specimens grown outdoors with 30% shade in Essex County, Mass., during the month of October.

1. FLOWER

Blooming habit: Near continuous.

A. Bud:
- (1) *Size.*—Medium.
- (2) *Form.*—Ovoid
- (3) *Color.*—When sepals first divide — 43C. When petals begin to unfurl — 43B at tips, 43C toward center. When half-blown: 43A shading to 43D and 4D at point of attachment. Reverse side of petals — 52A at tip shading to 52D and 4D at point of attachment.
- (4). *Sepals.*—About $\frac{1}{3}$ longer than bud and foliated with a feathery-appearing crest atop bud (sometimes referred to as "whiskered").
- (5) *Peduncle.*—Length — $1\frac{1}{4}$ inch. Aspect — straight, sturdy. Strength — erect, holds bloom upright. Color - 144A.

B. Bloom:
- (1) *Size.*—Average size when fully expanded — about $1\frac{1}{4}$ to $1\frac{1}{2}$ inches
- (2) *Borne.*—Sprays of 5 to 12 blooms and some borne singly.
- (3) *Form.*—High centered until full blown, petals reflexed and quill symmetrically.
- (4) *Petalage.*—Number of petals under normal conditions — about 50 to 55.
- (5) *Color.*—(during first 2 days). Inner petals at center of flower — 47B. Outer petals — 47B. Base of petals (point of attachment) — 4C. Reverse of petals — 52A at tip shading to 52D and white. General tonality from a distance — coral pink.
- (6) *Color change.*—As bloom ages — 43B shading to 52C and after three or more days to 53C giving a general soft coral pink tonality.

C. Petals:
- (1) *Texture.*—Thick.
- (2) *Appearance.*—Satiny inside and outside.
- (4) *Arrangement.*—Imbricated.
- (5) *Petaloids in center.*—Medium.
- (6) *Persistence.*—Drop off cleanly.
- (7) *Fragrance.*—None.
- (8) *Lasting quality.*—Very long lasting on plant and as cut flower.

2. REPRODUCTIVE ORGANS

A. Stamens, filaments and anthers:
(1) *Arrangement.*—Few, interspersed with petaloids.
(2) *Color.*—26A.
B. Pollen: None observed.
C. Styles: Uneven length.
D. Stigmas: Color — 45C.
E. Hips: None observed.

3. PLANT

A. Form: Upright, compact.
B. Growth: Vigorous, uniform branching. Height attained — 12 to 16 inches
C. Foliage: Compound 5 to 7 leaflets.
(1) *Size.*—Medium.
(2) *Quantity.*—Very abundant.
(3) *Color.*—New foliage: Upper side — near to 137A. Under side — near to and 139C. Old foliage: Upper side — 137C. Under side — 139C.
(4) *Shape.*—Ovoid pointed.
(5) *Texture.*—Upper side — matte, ribbed. Under side — matte, veined.
(6) *Edge.*—Serrated.
(7) *Serration.*—Compound, regular.

(8) *Leaf stem.*—Color — upper side — 178A. under side — 139C.
(9) *Stipules.*—Long, considerable bearding.
(10) *Resistance to disease.*—Blackspot — good. Mildew — good.
D. Wood:
(1) *New wood.*—Color — near 144A. Bark — smooth.
(2) *Old Wood.*—Color — 143A. Bark — smooth.
E. Thorns:
(1) *Thorns.*—Quantity: on main stalks and on laterals approximately 12 per 10 cm of length. Form — straight, long, thin, pointed. Length — medium. Color (when young) — 47D; (old) — 178A. Position — irregular.
(2) *Prickles.*—None.
F. Winter hardiness : Needs some protection in extreme climates.

I claim:

1. A new and distinct variety of rose plant of the miniature class, substantially as shown and described, characterized particularly by high centered, many petalled coral pink blooms borne both in sprays and singly supported erect on sturdy peduncles with petals reflexing and quilling symmetrically on opening which are long lasting on the plant and as cut flowers.

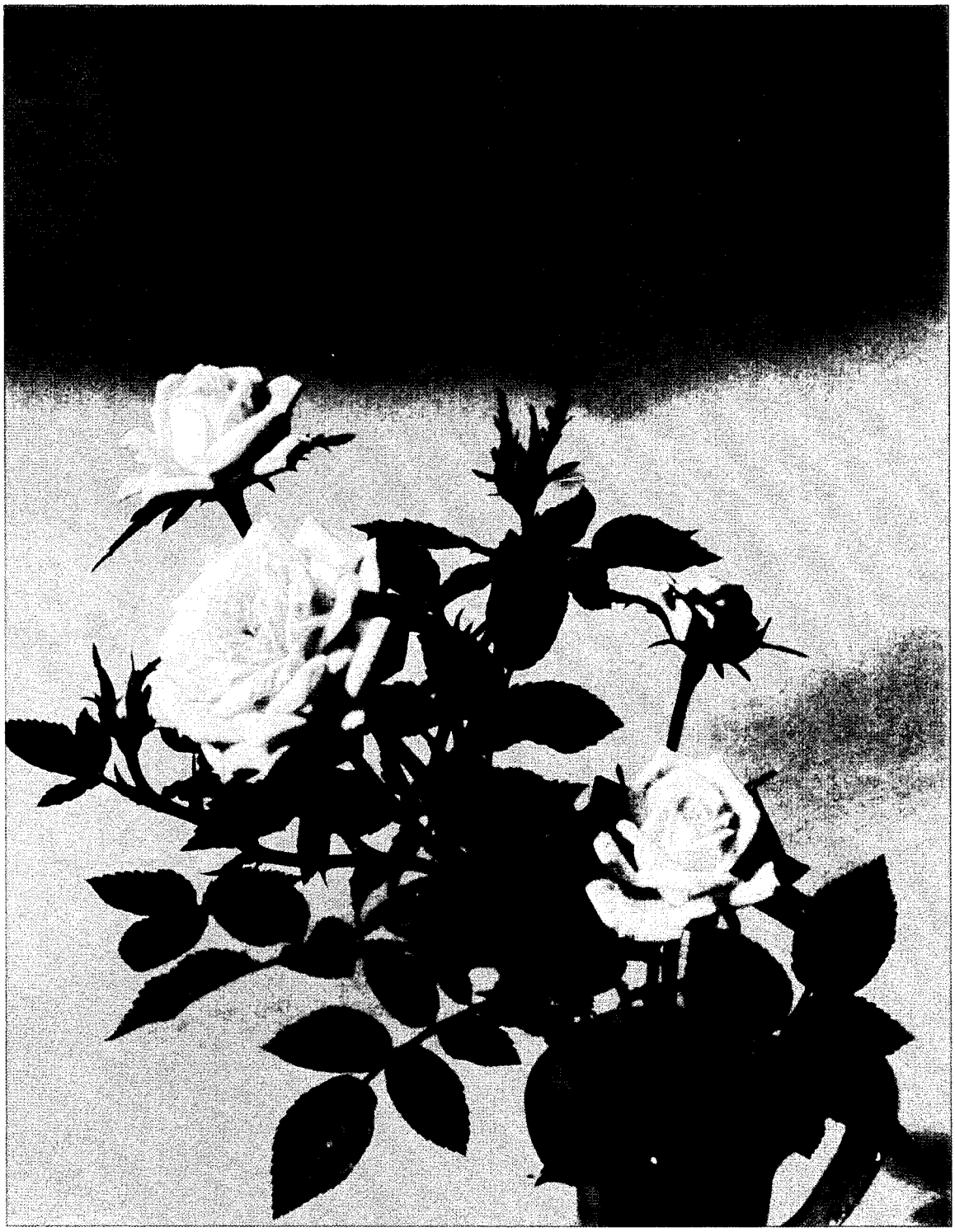

* * * * *